United States Patent
Schönrock et al.

[11] Patent Number: 5,804,167
[45] Date of Patent: Sep. 8, 1998

[54] EMULSIFIER-FREE, FINELY DISPERSE COSMETIC OR DERMATOLOGICAL FORMULATIONS OF THE WATER-IN-OIL TYPE

[75] Inventors: Uwe Schönrock, Norderstedt; Michael Christiansen, Tornesch; Sigrid Steinke, Hamburg, all of Germany

[73] Assignee: Beiersdorf AG, Hamburg, Germany

[21] Appl. No.: 724,939

[22] Filed: Oct. 2, 1996

[30] Foreign Application Priority Data

Oct. 24, 1995 [DE] Germany ............... 195 39 428.3

[51] Int. Cl.$^6$ ............... A61K 7/42; A61K 6/00; A61K 7/00
[52] U.S. Cl. ............... 424/59; 424/401; 514/937
[58] Field of Search ............... 424/59, 401; 514/937

[56] References Cited

U.S. PATENT DOCUMENTS 5,188,831  2/1993  Nicoll et al. ............... 424/401

FOREIGN PATENT DOCUMENTS

| 2374896 | 7/1978 | France . |
| 2686510 | 7/1993 | France . |
| 3027079 | 2/1982 | Germany . |
| 3430252 | 2/1986 | Germany . |
| 4201694 | 8/1992 | Germany . |
| 4338999 | 10/1994 | Germany . |
| 4425268 | 1/1996 | Germany . |
| 680565 | 9/1992 | Switzerland . |

OTHER PUBLICATIONS

Chemical Abstracts, vol. 112, No. 8, Feb. 19, 1990, Abstract No. 62371m, E. Willnska, et al., "Base for water–in–oil type cosmetic creams", p. 407.

Kosmetik Und Aerosol, Bd. 44, Nr. 24, Nov. 1971, pp. 932–935, V. Heitland, "Stabilitatsverbessernde Zusatze in Kosmetischen Emulsionen".

*Primary Examiner*—Kimberly Jordan
*Attorney, Agent, or Firm*—Sprung Kramer Schaefer & Briscoe

[57] ABSTRACT

Finely disperse, emulsifier-free cosmetic or dermatological formulations of the water-in-oil type, comprising oily phase comprising, as the main constituent, or more non-polar oils, fats and/or waxes, aqueous phase, or more salts of di- and/or trivalent metal cations and one or more alkylcarboxylic acids having 10–24 C atoms, and, if desired, comprising customary cosmetic or dermatological auxiliaries, additives and/or active compounds.

7 Claims, No Drawings

EMULSIFIER-FREE, FINELY DISPERSE COSMETIC OR DERMATOLOGICAL FORMULATIONS OF THE WATER-IN-OIL TYPE

DESCRIPTION

The present invention relates to cosmetic and dermatological formulations of the water-in-oil type, processes for their preparation and their use for cosmetic and medicinal purposes.

Cosmetic skin care is primarily to be understood as meaning that the natural function of the skin as a barrier against environmental influences (for example dirt, chemicals, microorganisms) and against the loss of endogenous substances (for example water, natural fats, electrolytes) is intensified or re-established.

If this function is impaired, an increased absorption of toxic or allergenic substances or attack by microorganisms and, as a consequence, toxic or allergic skin reactions may occur.

The aim of skin care is furthermore to compensate the loss of fats and water from the skin caused by daily washing. This is important precisely if the natural capacity for regeneration is inadequate. Skin care products should furthermore protect against environmental influences, in particular against sun and wind, and delay aging of the skin.

As a rule, medicinal topical compositions comprise one or more medicaments in an active concentration. For simplicity, to make a clear distinction between cosmetic and medicinal use and corresponding products, reference is made to the legal provisions of the Federal Republic of Germany (for example cosmetics legislation and foodstuffs and medical preparations law).

In simple emulsions, one phase contains finely disperse droplets of the second phase enclosed by an emulsifier shell (water droplets in W/O emulsions or lipid vesicles in O/W emulsions).

The use of customary cosmetic emulsifiers is acceptable in itself. Nevertheless, emulsifiers, like any chemical substance in the end, can cause allergic reactions or reactions based on hypersensitivity of the user in an individual case.

It is thus known that certain photodermatoses can be triggered by certain emulsifiers, and also by various fats, and at the same time exposure to sunlight. Such photodermatoses are also called "Mallorca acne". One object of the present invention was therefore to develop emulsifier-free sunscreen products.

Emulsifier-free light protection preparations based on so-called hydrodispersions have been accessible to the consumer for some time.

Hydrodispersions are dispersions of a liquid, semi-solid or solid internal (discontinuous) lipid phase in an external aqueous (continuous) phase.

In contrast to O/W emulsions, which are distinguished by a similar phase arrangement, hydrodispersions are essentially free from emulsifiers. Hydrodispersions, like other emulsions otherwise, are metastable systems and tend to convert into a state of two discrete phases which are coherent in themselves. In emulsions, the choice of a suitable emulsifier prevents phase separation.

In hydrodispersions of a liquid lipid phase in an external aqueous phase, the stability of such a system can be guaranteed, for example, by building up in the aqueous phase a gel matrix in which the lipid droplets are suspended in a stable form.

By converse analogy, W/O lipodispersions, to which the present invention relates, are emulsifier-free finely disperse formulations of the water-in-oil type.

Formulations of the prior art in general have the disadvantage that they are either unstable, have a narrow range of use or are limited to a limited choice of starting substances. It is usually furthermore the case that compositions of the prior art contain little or even no skin care fats or oils.

An object of the present invention was to prepare emulsifier-free finely disperse formulations of the water-in-oil type which do not have the disadvantages of the prior art. Another object of the invention was to enrich the limited range of emulsifier-free finely disperse formulations of the water-in-oil type of the prior art. It was furthermore an object of the present invention to provide stable, emulsifier-free formulations with a high fat and/or oil content.

Astonishingly, these objects are achieved by finely disperse, emulsifier-free cosmetic or dermatological formulations of the water-in-oil type comprising an oily phase comprising, as the main constituent, one or more non-polar oils, fats and/or waxes, an aqueous phase, one or more salts of di- and/or trivalent metal cations and one or more alkylcarboxylic acids having 10–24 C atoms, and, if desired, comprising customary cosmetic or dermatological auxiliaries, additives and/or active compounds.

The aluminium stearates are salts, which are advantageous according to the invention, of di- and/or trivalent metal cations and one or more alkylcarboxylic acids having 10 –24 C atoms.

The non-polar fats, waxes and oils according to the invention are advantageously chosen from the group consisting of vaseline (petrolatum), paraffin oil and polyolefins. Among the polyolefins, polydecenes are the preferred substances.

It is furthermore possible and advantageous to incorporate an additional content of silicone oils into the formulations according to the invention.

Formulations according to the invention advantageously comprise 0.5–50% by weight of one or more non-polar oils, fats and/or waxes, 0.005–10% by weight of one or more salts of di- and/or trivalent metal cations and one or more alkylcarboxylic acids having 10– 24 C atoms, if appropriate auxiliaries, additives or active compounds, and water.

Formulations according to the invention particularly advantageously comprise 0.5–50% by weight of petrolatum, 0.005–10% by weight of one or more salts of di- and/or trivalent metal cations and one or more alkylcarboxylic acids having 10–24 C atoms, if appropriate auxiliaries, additives or active compounds, and water. Formulations according to the invention also particularly advantageously comprise 0.5–50% by weight of paraffin oil, 0.005–10% by weight of one or more salts of di- and/or trivalent metal cations and one or more alkylcarboxylic acids having 10–24 C atoms, if appropriate auxiliaries, additives or active compounds, and water.

Formulations according to the invention especially advantageously comprise 0.5–30% by weight of petrolatum, 0.5–30% by weight of paraffin oil, 0.005 –10% by weight of one or more salts of di- and/or trivalent metal cations and one or more alkylcarboxylic acids having 10–24 C atoms, if appropriate auxiliaries, additives or active compounds, and water.

Formulations according to the invention preferably comprise 1.5–20% by weight of petrolatum, 3–18% by weight of paraffin oil, 0.1–2% by weight of one or more salts of di- and/or trivalent metal cations and one or more alkylcarboxylic acids having 10–24 C atoms, if appropriate auxiliaries, additives or active compounds, and water.

Formulations according to the invention particularly preferably comprise 5–10% by weight of petrolatum, 8–18% by weight of paraffin oil, 0.1–2% by weight of one or more salts of di- and/or trivalent metal cations and one or more alkylcarboxylic acids having 10–24 C atoms, if appropriate auxiliaries, additives or active compounds, and water.

If appropriate, the aqueous phase of the formulations according to the invention advantageously comprises alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol or glycerol, and, in particular, one or more thickening agents, which can advantageously be chosen from the group consisting of silicon dioxide, aluminium silicates, polysaccharides and derivatives thereof, for example hyaluronic acid, xanthan gum and hydroxypropylmethyl-cellulose, particularly advantageously from the group consisting of polyacrylates, preferably a polyacrylate from the group of so-called carbopols, for example carbopols of types 980, 981, 1382, 2984 or 5984, or also of the ETD (easy-to-disperse) types 2001, 2020 and 2050, in each case individually or in any desired combinations with one another.

Particularly advantageous formulations are furthermore obtained if antioxidants are employed as additives or active compounds. According to the invention, the formulations advantageously comprise one or more antioxidants. All the antioxidants suitable or customary for cosmetic and/or dermatological uses can be used as antioxidants which are favourable but nevertheless are to be used optionally.

The antioxidants are advantageously chosen from the group consisting of amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphox-imines, homocysteine-sulphoximine, buthionine-sulphones and penta-, hexa- and heptathionine-sulphoximine) in very low tolerated dosages (for example pmol to μmol/kg), and furthermore (metal) chelators (for example α-hydroxy-fatty acids, palmitic acid, phytic acid or lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, butylhydroxy-toluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives, which are suitable according to the invention (salts, esters, ethers, sugars, nucleotides, nucleosides, peptides and lipids), of these active compounds mentioned.

Oil-soluble antioxidants can be particularly advantageously employed in the context of the present invention.

An astonishing property of the present invention is that formulations according to the invention are very good vehicles for cosmetic or dermatological active compounds in the skin, preferred active compounds being antioxidants which can protect the skin against exposure to oxidation. Preferred antioxidants here are vitamin E and derivatives thereof and vitamin A and derivatives thereof.

The amount of antioxidants (one or more compounds) in the formulations is preferably 0.001–30% by weight, particularly preferably 0.05–20% by weight, in particular 1–10% by weight, based on the total weight of the formulation.

If vitamin E and/or derivatives thereof is/are the antioxidant or antioxidants, it is advantageous to choose the particular concentrations thereof from the range from 0.001–10% by weight, based on the total weight of the formulation.

If vitamin A or vitamin A derivatives or carotenes or derivatives thereof is/are the antioxidant or antioxidants, it is advantageous to choose the particular concentrations thereof from the range from 0.001–10% by weight, based on the total weight of the formulation.

It is of course known to the expert that high-quality cosmetic formulations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellents, alcohol, water, salts, substances having an antimicrobial, proteolytic or keratolytic action and the like.

Mutatis mutandis, corresponding requirements apply to the formulation of medicinal formulations.

Depending on their build-up, the formulations according to the invention can accordingly be used, for example, as skin protection cream, cleansing milk, sunscreen lotion, nutrient cream, vanishing cream or night cream and the like. Where appropriate, it is possible and advantageous to use the formulations according to the invention as a base for pharmaceutical formulations.

Those cosmetic and dermatological formulations which are in the form of a sunscreen agent are also favourable. These preferably additionally comprise at least one UVA filter substance and/or at least one UVB filter substance and/or at least one inorganic pigment, in addition to the active compound combinations according to the invention.

However, it is also advantageous in the context of the present inventions to compose those cosmetic and dermatological formulations of which the chief purpose is not protection from sunlight but which nevertheless comprise a content of UV protection substances. Thus, for example, UV-A or UV-B filter substances are usually incorporated into vanishing creams.

UV protection substances, like antioxidants and, if desired, preservatives, also represent active protection of the formulations themselves against decay.

Formulations according to the invention can furthermore advantageously comprise substances which absorb UV radiation in the UVB range, the total amount of filter substances being, for example, 0.1% by weight to 30% by weight, preferably 0.5–10% by weight, in particular 1.0–6.0% by weight, based on the total weight of the formulations, in order to provide cosmetic formulations which protect the hair or skin from the entire range of ultraviolet radiation. They can also be used as sunscreen agents for the hair or skin.

If the emulsions according to the invention comprise UVB filter substances, these can be oil-soluble or water-soluble. Oil-soluble UVB filters which are advantageous according to the invention are, for example:

3-benzylidenecamphor derivatives, preferably 3-(4-methylbenzylidene)camphor and 3-benzylidene- camphor;

4-aminobenzoic acid derivatives, preferably 2-ethyl- hexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'- methylbenzophenone and 2,2'-dihydroxy-4-methoxybenzophenone;

esters of benzalmalonic acid, preferably di(2-ethyl-hexyl) 4-methoxybenzalmalonate;

2,4,6-trianilino-(p-carbo-2'-ethyl-1'-hexyloxy)-1,3,5-triazine.

Advantageous water-soluble UVB filters are, for example:

salts of 2-phenylbenzimidazole-5-sulphonic acid, such as its sodium, potassium or its triethanol-ammonium salt, and 2-phenylbenzimidazole-5-sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4- (2-oxo-3-bornylidenemethyl)-benzenesulphonic acid, 2-methyl-5-(2-oxo-3-bornylidenemethyl)benzenesulphonic acid and their salts.

The list of UVB filters mentioned, which can be used in combination with the active compound combinations according to the invention, is of course not intended to be limiting.

It may also be advantageous to formulate lipodispersions according to the invention with UVA filters which have usually been contained in cosmetic formulations to date. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1, 3-dione.

Cosmetic and dermatological formulations according to the invention can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide.

The cosmetic and dermatological formulations according to the invention can furthermore comprise cosmetic auxiliaries such as are usually used in such formulations, for example preservatives, bactericides, virucides, perfumes, substances for preventing foaming, dyestuffs, pigments which have a colouring action, thickening agents, surface-active substances, emulsifiers, softening, moistening and/or humectant substances, anti-inflammatory substances, medicaments, fats, oils, waxes or other customary constituents of a cosmetic or dermatological formulation, such as alcohols, polyols, polymers, foam stabilizers, electrolytes or organic solvents.

Further constituents which can be used are:

fats, waxes and other natural and synthetic fat substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

The following example is intended to illustrate the present invention.

|  | % by weight |
|---|---|
| dimethicone | 2.00 |
| phenyltrimethicone | 4.00 |
| petrolatum DAB 10 | 10 00 |
| polydecene | 30.00 |
| $C_{12-15}$-alkyl benzoate | 3.00 |
| octoxyglycerol | 1.00 |
| butylene glycol | 5.00 |
| aluminium stearate | 0.80 |
| behenyl alcohol | 4.00 |
| hydrogenated castor oil | 4.00 |
| bisabolol | 0.10 |
| water, demineralized | to 100.00 |

We claim:

1. Finely disperse, emulsifier-free cosmetic or dermatological formulations of the water-in-oil type, comprising an oily phase comprising, as the main constituent, one or more non-polar fats or waxes, an aqueous phase, one or more salts of di- or trivalent metal cations and one or more alkylcarboxylic acids having 10–24 C atoms, and, optionally, comprising cosmetic or dermatological auxiliaries, additives or active compounds.

2. Formulations according to claim 1, characterized in that one or more aluminium stearates are chosen as the salt or salts of di- or trivalent metal cations and one or more alkylcarboxylic acids having 10–24 C atoms.

3. Formulations according to claim 1, characterized in that the oils, fats and waxes are chosen from the group consisting of vaseline (petrolatum), paraffin oil and polyolefins.

4. Formulations according to claim 1, comprising 0.5–50% by weight of one or more non-polar oils, fats or waxes, 0.005–10% by weight of one or more salts of di- or trivalent metal cations and one or more alkylcarboxylic acids having 10–24 C atoms, optionally auxiliaries, additives or active compounds, and water.

5. Formulations according to claim 1, comprising 0.5–50% by weight of petrolatum, 0.00–10% by weight of one or more salts of di- or trivalent metal cations and one or more alkylcarboxylic acids having 10–24 C atoms, optionally auxiliaries, additives or active compounds, and water.

6. In a method for transporting active compounds into the skin the improvement which comprises employing the formulations according to claim 1 as the cosmetic or dermatological vehicle.

7. The method according to claim 6, wherein the active compound is an antioxidant.

* * * * *